(12) United States Patent  
Hoefig

(10) Patent No.: US 8,002,699 B2  
(45) Date of Patent: Aug. 23, 2011

(54) ENDOSCOPE AND METHOD FOR FIXING OPTICAL FIBERS THEREIN

(75) Inventor: Siegfried Hoefig, Muehlheim (DE)

(73) Assignee: Karl Storz GmbH & Co. KG (DE)

( * ) Notice: Subject to any disclaimer, the term of this patent is extended or adjusted under 35 U.S.C. 154(b) by 894 days.

(21) Appl. No.: 11/505,173

(22) Filed: Aug. 16, 2006

(65) Prior Publication Data

US 2007/0092188 A1   Apr. 26, 2007

Related U.S. Application Data

(63) Continuation of application No. PCT/EP2005/001577, filed on Feb. 16, 2005.

(30) Foreign Application Priority Data

Feb. 16, 2004   (DE) .......................... 10 2004 008 458

(51) Int. Cl.
    *A61B 1/00*   (2006.01)
(52) U.S. Cl. ......... 600/132; 600/178; 600/182; 385/117
(58) Field of Classification Search ............... 600/132, 600/178, 182; 385/117
    See application file for complete search history.

(56) References Cited

U.S. PATENT DOCUMENTS

| | | | | |
|---|---|---|---|---|
| 3,897,134 A * | 7/1975 | Scrivo et al. | ..................... | 385/78 |
| 4,313,431 A | 2/1982 | Frank | ................. | 128/7 |
| 4,341,205 A * | 7/1982 | Hosono et al. | ................. | 600/133 |
| 4,350,150 A | 9/1982 | Kubota et al. | ..................... | 128/6 |
| 4,416,268 A * | 11/1983 | Hagino | .......................... | 600/132 |
| 4,779,613 A * | 10/1988 | Hashiguchi et al. | .......... | 600/169 |
| 5,193,135 A * | 3/1993 | Miyagi | .......................... | 385/117 |
| 5,359,453 A * | 10/1994 | Ning | .......................... | 359/435 |
| 5,599,278 A * | 2/1997 | Hibbard | ........................ | 600/133 |
| 5,601,525 A * | 2/1997 | Okada | ........................... | 600/160 |
| 5,746,494 A * | 5/1998 | Koeda et al. | ..................... | 362/560 |
| 5,797,836 A * | 8/1998 | Lucey et al. | ................... | 600/109 |
| 5,954,637 A * | 9/1999 | Francis | .......................... | 600/138 |
| 6,085,011 A | 7/2000 | Klausmann et al. | ........... | 385/115 |
| 6,346,076 B1 * | 2/2002 | Rovegno | ........................ | 600/173 |
| 6,419,628 B1 * | 7/2002 | Rudischhauser et al. | ...... | 600/161 |
| 6,478,478 B1 * | 11/2002 | Campbell | ........................ | 385/89 |

(Continued)

FOREIGN PATENT DOCUMENTS

DE   197 32 051   5/1998

(Continued)

OTHER PUBLICATIONS

English translation of the International Preliminary Report on Patentability, Oct. 4, 2006, 11 Pages.

(Continued)

*Primary Examiner* — Matthew J Kasztejna
(74) *Attorney, Agent, or Firm* — St. Onge Steward Johnston & Reens LLC

(57) ABSTRACT

An endoscope has a shaft, a head disposed at a proximal end of said shaft and a light connection disposed at said head. Optical fibers extend from said proximal light connection to a distal end of said shaft. A sleeve in which a proximal end section of said light fibers is fixed is designed in such a way that it can be introduced in a linear movement without turning it into the light connection. Said sleeve is axially movable in said connecting piece.

6 Claims, 6 Drawing Sheets

U.S. PATENT DOCUMENTS

| | | | |
|---|---|---|---|
| 6,503,196 B1 * | 1/2003 | Kehr et al. | 600/176 |
| 6,589,165 B2 * | 7/2003 | Bodor et al. | 600/172 |
| 6,626,582 B2 * | 9/2003 | Farrar et al. | 385/53 |
| 6,716,161 B2 * | 4/2004 | Higuma et al. | 600/133 |
| 6,955,644 B2 * | 10/2005 | Forkey et al. | 600/133 |
| 2005/0143626 A1 * | 6/2005 | Prescott | 600/162 |

FOREIGN PATENT DOCUMENTS

| | | |
|---|---|---|
| DE | 298 05 720 | 9/1999 |
| DE | 199 42 152 | 3/2000 |
| DE | 101 64 582 | 6/2003 |
| EP | 0 072 193 | 2/1983 |
| EP | 0 072 194 | 2/1983 |
| GB | 2 342 462 | 4/2000 |

OTHER PUBLICATIONS

International Search Report; May 19, 2005; 8 pages.

* cited by examiner

ENDOSCOPE AND METHOD FOR FIXING OPTICAL FIBERS THEREIN

CROSS-REFERENCE OF RELATED APPLICATION

This application is a continuation of pending international application PCT/EP 2005/001577 filed on Feb. 16, 2005 which designates U.S. and which claims priority of German patent application No. 10 2004 008 458.0 filed on Feb. 16, 2004.

BACKGROUND OF THE INVENTION

The present invention relates to an endoscope and to a method for fixing optical fibers therein.

Endoscopes usually comprise a shaft and a head disposed at a proximal end of the shaft. A light connection is disposed at the head and optical fibers are provided which extend from said proximal light connection to a distal end of said shaft for guiding light from said proximal light connection to said distal end of the shaft. A sleeve is usually provided in which a proximal end section of the light fibers is fixed. The sleeve containing the fixed end section of the light fibers is introduced into a connecting piece of said light connection.

The light fibers are usually made of glass fibers which tend to crack if the sleeve is turned in in a screw-like motion into the connecting piece.

A break of individual fibers leads to a reduction in the quantity of the light that is guided. Furthermore, putting the optical fibers under tensile stress can additionally lead to damage the optical fibers. That is further accelerated by the fact that the medicine endoscopes must be regularly autoclaved in which case they are heated briefly to temperatures above 150° C. and are very quickly cooled thereafter. This results in different expansion of parts of the endoscope that are produced from various materials. This can amplify the stresses on the optical fibers and can lead to further damage in the optical fibers, for example, when the shaft of the endoscope expands more strongly than the optical fibers contained therein.

It is therefore an object of the present invention to provide an endoscope with less stress acting on the optical fibers.

It is a further object of the invention to provide an endoscope with high light guide properties for a long term.

It is a further object of the invention to provide a method for fixing optical fibers in an endoscope resulting in less stressed optical fibers.

It is a further object of the invention to provide a method for fixing optical fibers in an endoscope with a long duration of high light guiding properties.

SUMMARY OF THE INVENTION

These objects are achieved by an endoscope comprising a shaft, a head disposed at a proximal end of said shaft, a light connection provided at said head, optical fibers extending from said proximal light connection to a distal end of said shaft for guiding light from said proximal light connection to said distal end, and having a sleeve in which a proximal end section of said light fibers is fixed, said sleeve is designed in such a way, that it can be introduced into a connecting piece of said light connection in a linear movement without turning it, and wherein said sleeve is axially movable in said connecting piece.

These objects are further achieved by a method for fixing optical fibers in an endoscope having a shaft, a head disposed at a proximal end of said shaft, a light connection provided at said head, optical fibers extending from said proximal light connection to a distal end of said shaft for guiding light from said proximal light connection to said distal end, and a sleeve in which a proximal end section of said light fibers is fixed, comprising the steps of introducing a proximal end section of optical fibers into a sleeve, introducing said sleeve by a linear movement without turning it in a direction of its longitudinal axis into a connecting piece of a light connection of said light connection, fixing said proximal end section of said optical fibers in said sleeve, wherein said sleeve is introduced in two steps into said connecting piece, in a first step into a first position in which said sleeve is in a press-fit within the connecting piece and transferring it into a second position, pushed further into the connecting piece, in which second position said sleeve is axially movable in said connecting piece.

The introduction by means of a linear movement can be performed in this case by simply plugging the sleeve into the connecting piece. However, it is also possible to fit on the connecting piece a rotatable bayonet lock, for example, that cooperates with a pin fitted on the sleeve such that the sleeve is pushed linearly into the connecting piece by rotating the bayonet lock.

It is common to all the abovenamed embodiments that the sleeve executes a linear movement in the direction of its longitudinal axis.

It has emerged that when the sleeve is introduced into the connecting piece by a linear movement, twisting of the optical fibers no longer comes about. It is thereby possible to avoid breaking of individual fibers.

It has further emerged that the optical fibers fixed in the sleeve are relieved of tension by introducing the sleeve by a linear movement. The optical fibers running in the interior of the endoscope are in this case pushed a little into the endoscope. As a result, a kind of loop or arc is present by which expansion stresses occurring during use can be at least mitigated, if not even completely compensated.

It is therefore possible to mount optical fibers in the light connection of an endoscope without damage and with a substantially lesser loading.

Since the sleeve is housed within the connecting piece axially movable, thermal or mechanical stresses acting on the connecting piece can be charged by a movement of the sleeve in a certain extent. Additionally, manufacturing tolerances can be compensated due to that axial movement of that sleeve within the connecting piece.

In terms of one configuration of the invention, the method has two further steps, specifically disconnecting an end piece of the sleeve together with the optical fibers contained therein; and processing an end surface of the sleeve and the optical fibers contained therein.

This measure provides in a simple way a plane end surface at the sleeve and the optical fibers.

After the end surface has been processed, for example by grinding and polishing, a means for coupling in light can be mounted in a planar fashion on the sleeve and the optical fibers, and this leads to the light being coupled in with a high light yield.

Furthermore, it is possible by means of this measure to use sleeves that are longer than the connecting piece, and this facilitates the introduction of the sleeve. Disconnecting a part of the sleeve projecting from said connecting piece ensures that the sleeve and the optical fibers terminate in a planar fashion in the finished light connection.

The sleeve is introduced in two stages, specifically introducing it in a first position in which the sleeve is pressed into the connecting piece, and then transferring it into a second position, pushed further in, in which the sleeve is captured in an axially movable fashion in the connecting piece.

Owing to the above measure, it is possible to fix the sleeve firstly in the connecting piece such that manipulations can be carried out at the sleeve or at the proximal end section of the optical fibers that is introduced therein. In particular, it is possible thereby for the optical fibers and, if appropriate, a part of the sleeve, to be cut to length and for the end surface to be ground and polished, while this end surface is still projecting beyond the connecting piece to a certain extent.

Thereafter, the sleeve can be transferred into a second position in which it is captured in the connecting piece in an axially movable fashion. This axial mobility permits, for example, manufacturing tolerances such as can occur during cutting up of the optical fibers to length or when grinding and polishing the end surface, to be compensated, and thereby renders it possible to apply a means for coupling light into the optical fibers in a planar fashion to the end surface.

In a further refinement of the invention, a resilient element is provided that cooperates with the sleeve in such a way that the latter is axially spring-loaded.

This resilient element has the advantage that it is possible thereby to press the sleeve with the optical fibers fixed therein against a means for coupling light into the optical fibers, and thereby it is ensured that the end surface bears against this means as accurately and in as planar a fashion as possible.

The provision of this resilient element has, moreover, the advantage that it is thereby possible to compensate stresses occurring during use of the endoscope, for example owing to thermal expansion. The loads exerted on the optical fibers are thereby reduced, in turn.

In a further refinement of the abovenamed measure, the resilient element is designed as an O-ring.

An O-ring has proved to be a particularly simple and cost effective embodiment of the resilient element. An O-ring further has the advantage that, apart from acting as a resilient element, it simultaneously also acts as a seal between the sleeve and the connecting piece. Consequently, for example, the possibility is avoided of vapor penetrating during autoclaving.

In a further refinement of the invention, the method has a further step, specifically fitting a fiber cone in such a way that the latter bears against the end surface.

The bundle of the optical fibers used for guiding light in the endoscope generally has a very small diameter because of the fact that the shaft of the endoscope is normally relatively thin, This renders it difficult to couple an adequate quantity of light directly into the optical fibers. A fiber cone cable serves the purpose in this case of greatly increasing the quantity of light coupled in.

In a further refinement of the abovenamed measure, an optically conductive medium is introduced between the end surface and the fiber cone.

It has emerged that despite high accuracy in the production, a minor gap remains between the end surface and the fiber cone. This gap reduces the effectiveness of the transmission of the light from the fiber cone to the end surface, and thus the effectiveness with which light is coupled into the optical fibers. It has now emerged that introducing an optically conductive medium between the end surface and the fiber cone can substantially increase the effectiveness of the transmission of light from the fiber cone into the optical fibers.

It is, however, possible by means of this measure for optical fibers fixed in sleeves to be prefabricated for storage.

In a further refinement of the invention, the proximal end region of the glass fibers is fixed in the sleeve by adhesive bonding.

Adhesive bonding has proved to be a simple, reliable and quick technique for fixing the optical fibers in the sleeve.

It goes without saying that the abovenamed features, and those still to be explained below, can be applied not only in the respectively specified combination, but also in other combinations, or on their own, without departing from the framework of the present invention.

BRIEF DESCRIPTION OF THE DRAWINGS

An exemplary embodiment of the invention is illustrated in the drawing and will be explained in more detail in the following description. In the drawing.

DETAILED DESCRIPTION OF A PREFERRED EMBODIMENT

Figure 1:
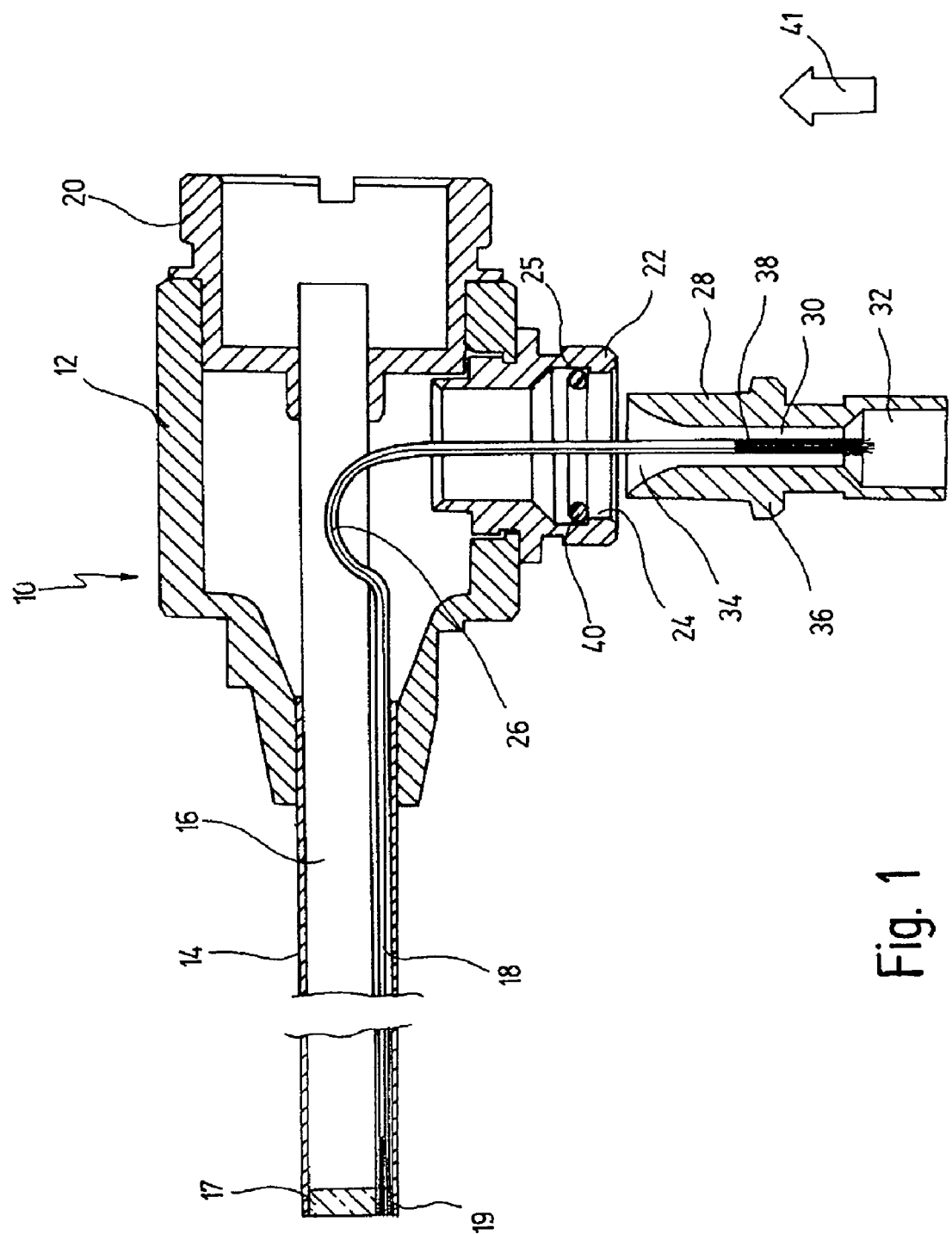
FIG. 1 shows a longitudinal section through an endoscope in a first mounting state, in which the sleeve has not yet been introduced into the connecting piece.

An endoscope is denoted in FIG. 1 in its entirety with the reference numeral 10.

The endoscope 10 has a head 12 which is adjoined distally by a shaft 14. The shaft 14 is illustrated here only partially.

Running in the shaft 14 is an optics tube 16. This optics tube 16 serves the purpose of holding the optical system, a multiplicity of rod lenses (not illustrated here) being held in the optics tube 16. The optics tube 16 is hermetically sealed at the distal end of the shaft 14 by a window 17.

Running parallel to the optics tube 16 in the shaft 14 are optical fibers 18 that are combined here to form a bundle. The optical fibers 18 are fixed at the distal end of the shaft 1.4 by means of an adhesive bonding site 19.

Adjoining the head 12 at the proximal side is a bushing 20 that serves the purpose of connecting to the optics tube 16 a means for imaging such as, for example, an eyepiece or a video camera.

Arranged, furthermore, at the head 12 is a connecting piece 22 that forms part of a light connection of the endoscope 10.

The longitudinal axis of the connecting piece 22 runs approximately at a right angle to the optics tube 16 such that the light connection does not impair the way the means for imaging is connected to the bushing 20.

In its outer end region, the connecting piece 22 has on its inner side an annular flange 24 adjoined by an undercut 25 in the direction of the head 12 of the endoscope 10.

The optical fibers 18 pass out of the head 12 of the endoscope 10 through the connecting piece 22. Here, the optical fibers 18 are laid in an arc 26 between the shaft 14 and the connecting piece 22, that is to say in the head 12.

A sleeve 28 that is intended to be pushed into the connecting piece 22 is illustrated in FIG. 1.

In the longitudinal direction, the sleeve 28 has a continuous bore 30 that widens at a distance from the endoscope into a first widened portion 32, and that widens near the endoscope into a second, funnel-shaped widened portion 34.

The sleeve 28 has an annular flange 36 on its outer side.

A proximal end section 38 of the optical fibers 18 is introduced into the bore 30 of the sleeve 28. In this case, the sleeve 28 has been pushed over the laterally projecting, proximal end of the optical fibers. The funnel-shaped widened portion 34 near the endoscope here facilitates the introduction of the proximal end region 38 of the optical fibers 18 into the bore 30 of the sleeve 28.

An O-ring 40 made from elastic material is arranged in the undercut 25 of the connecting piece 22.

The sleeve 28 is now introduced into the connecting piece 18 by a linear movement in the direction of its longitudinal axis, which is indicated by the arrow 41.

Figure 2:
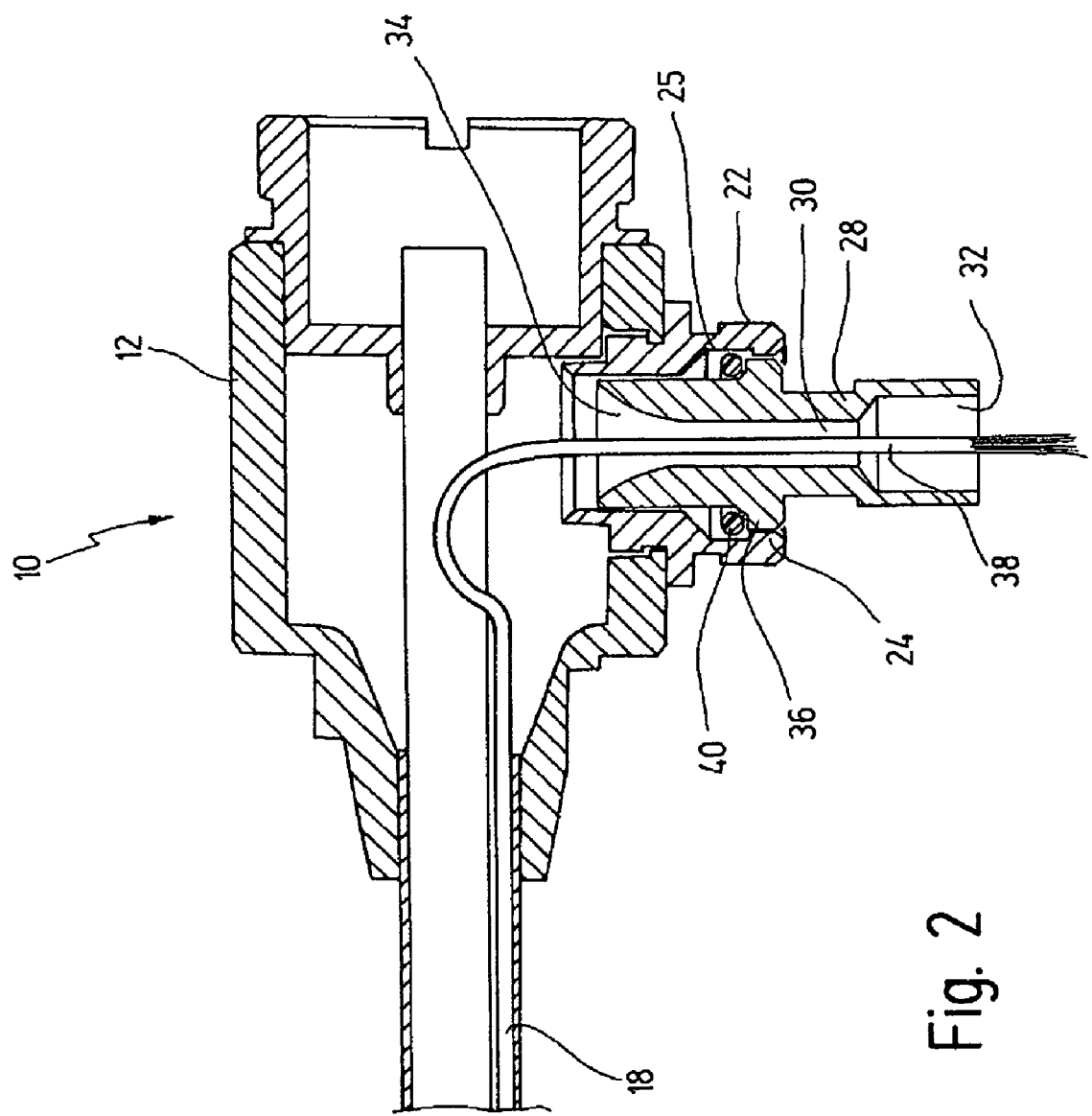
FIG. 2 shows a section of the endoscope of FIG. 1, the sleeve having been introduced into the connecting piece of the endoscope.

FIG. 2 illustrates a section of the endoscope 10 after the sleeve 28 has been introduced as indicated in FIG. 1 by the arrow 41.

The sleeve 28 is pushed into the connecting piece 22 so far that the annular flange 36 of the sleeve 28 comes to lie against the inner annular flange 24 of the connecting piece 22.

The annular flange 36 of the sleeve 28 cooperates with the annular flange 24 of the connecting piece 22 in such a way that the sleeve 28 is fixed in the position illustrated by frictional grip or a press fit.

Figure 3:
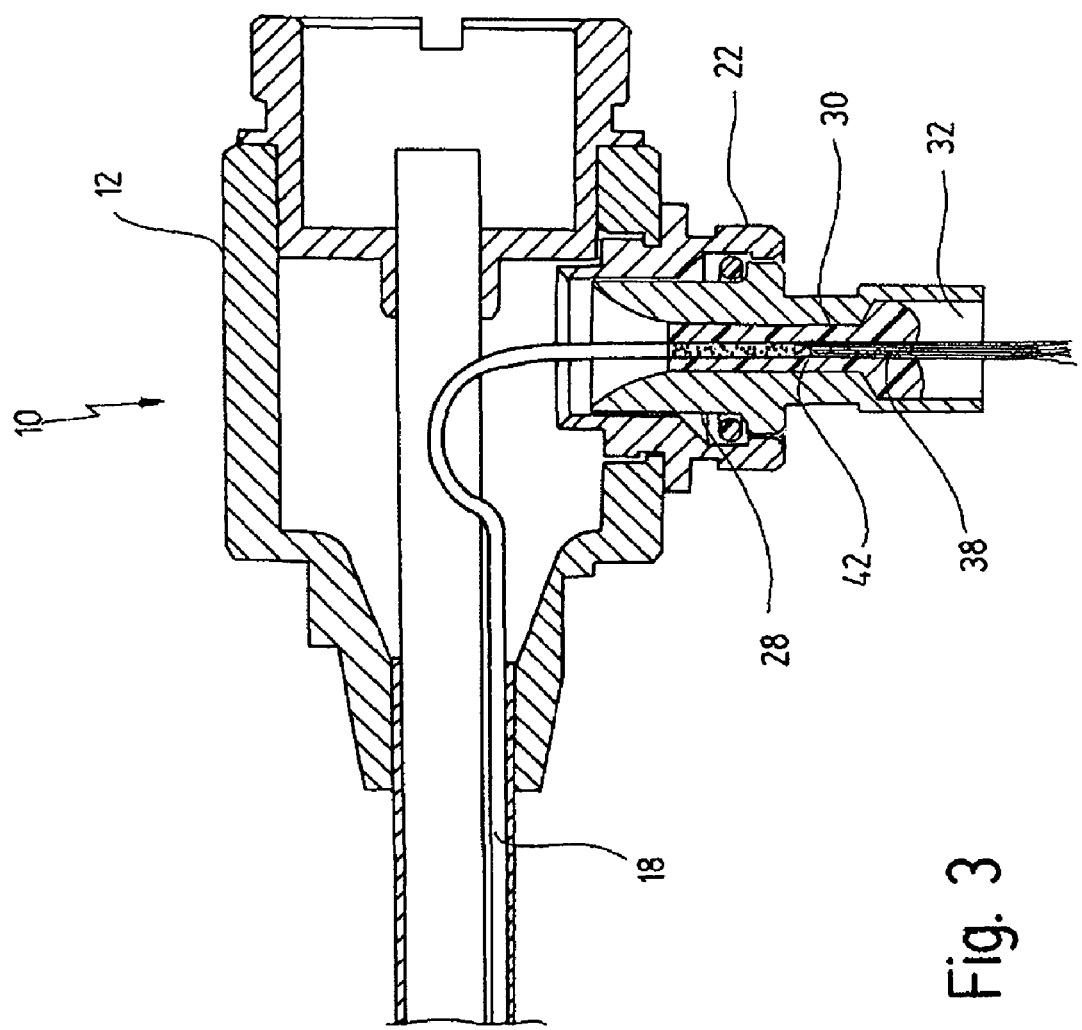
FIG. 3 shows the section of FIG. 2, the optical fibers having been fixed in the sleeve.

A subsequent mounting step is illustrated in FIG. 3. In this step, the proximal end sections 38 of the optical fibers 18 are fixed in the bore 30 of the sleeve 28. This is done by introducing an adhesive composition 42 into the bore 30. The introduction of the adhesive composition 42 into the bore 30 is facilitated here by the widened portion 32 at a distance from the endoscope. The adhesive composition 42 also penetrates the bundle of the optical fibers 18.

The adhesive composition 42 is cured, and this leads to a lasting and tight seal between the proximal end section 38 of the optical fibers 18 and the sleeve 28 as well as the optical fibers 18 among one another.

Figure 4:
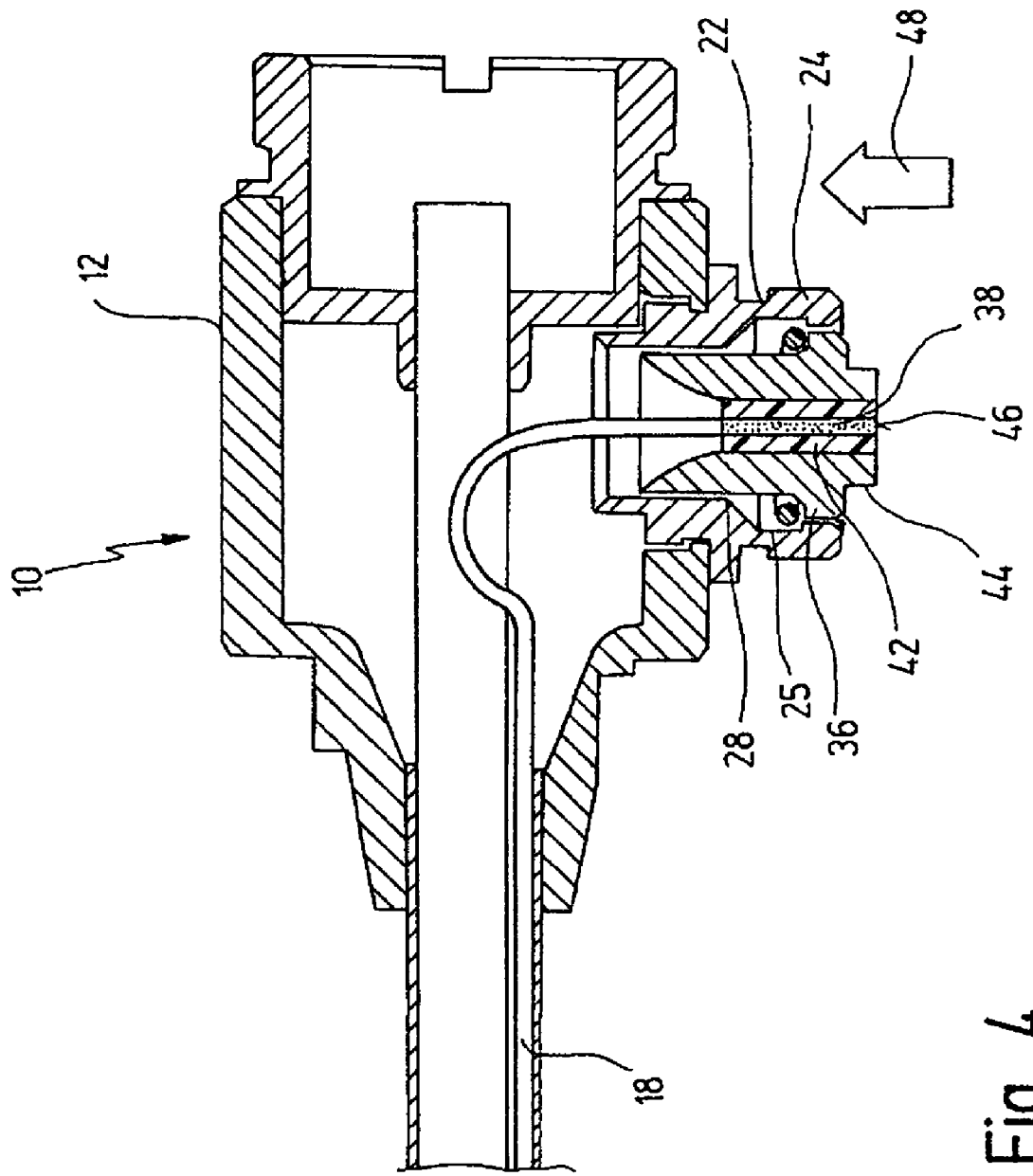
FIG. 4 shows the section of FIG. 3, the optical fibers having been cut to length.

FIG. 4 illustrates the section of the endoscope 10 of FIG. 3, the sleeve 28 with the proximal end region 38, fixed therein, of the optical fibers 18 being cut to length.

Here, cutting to length is performed such that a section 44 of the sleeve 28 and the optical fibers 18 contained therein remains projecting beyond the connecting piece 22.

Cutting to length has formed an end surface 46 at the proximal end section 38 of the optical fibers 18 and the sleeve 28. This end surface 46 is further processed, specifically ground and polished, in order to ensure that light is coupled into the optical fibers 18 as effectively as possible.

The sleeve 28 is fixed during these treatments in the connecting piece 22 due to the press-fitting in the connecting piece 22, that is to say the pressure exerted by the annular flange 36 of the sleeve 28 against the annular flange 24 of the connecting piece 22 during the process of cutting to length, grinding and polishing. Consequently, the manipulations on the sleeve 28 and the optical fibers 18 can be carried out reliably.

In a subsequent step, the sleeve 28 together with the proximal end section 38, contained therein, of the optical fibers 18 is now pushed further into the connecting piece 22 in the direction of the arrow 48. The annular flange 36 of the sleeve 28 is thereby moved into the undercut 25 of the connecting piece 22. This process of pushing in is also performed by a linear movement, as is indicated by the arrow 48.

Figure 5:
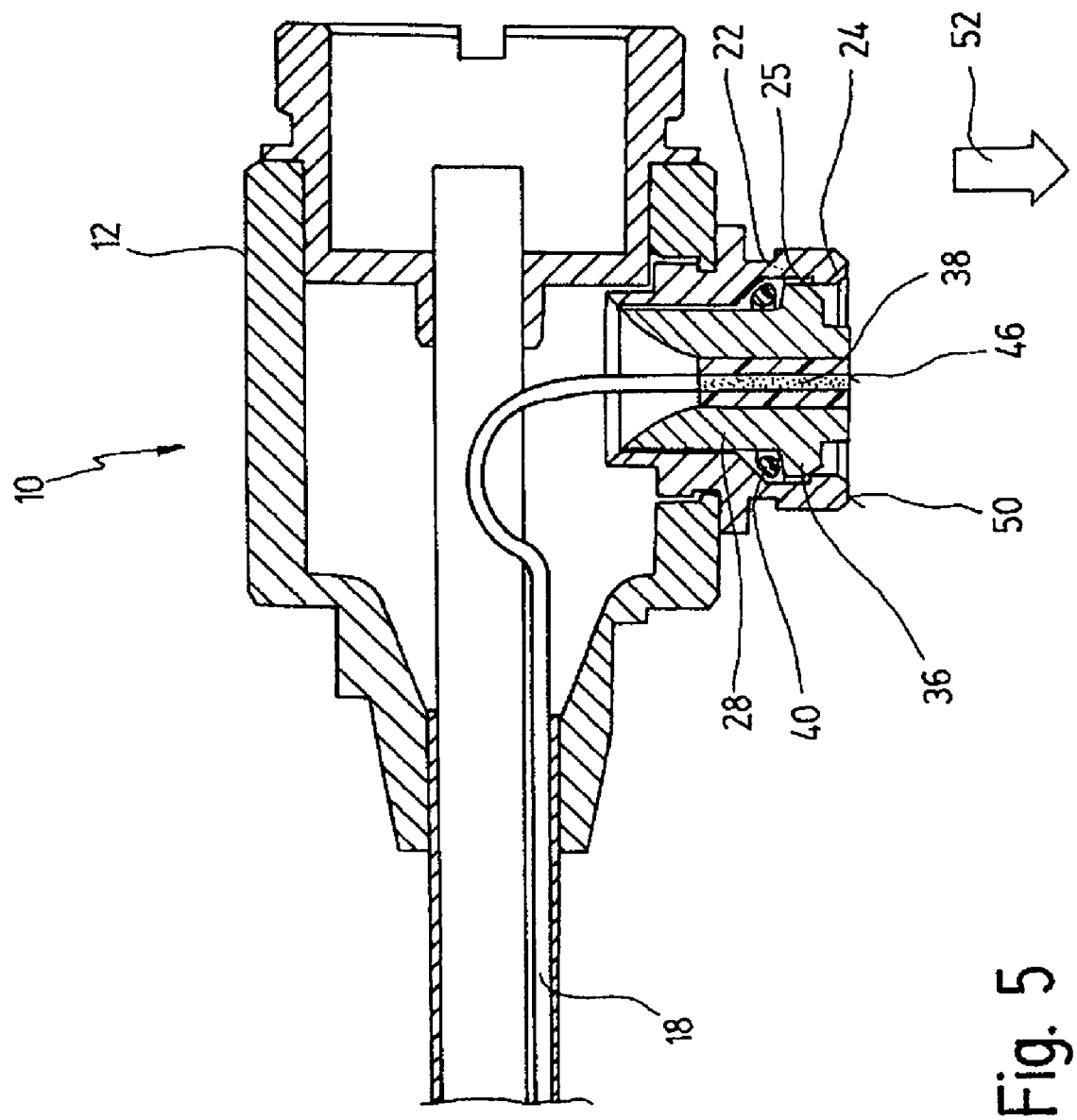
FIG. 5 shows the section of FIG. 4, the sleeve having been introduced into a second position.

It is to be seen in FIG. 5 that the annular flange 36 has been moved into the undercut 25 of the connecting piece 22. In said second position, the sleeve 28 is captured axially movable in said connecting piece 22.

The end surface 46 of the sleeve 28, or the proximal end section 38 of the optical fibers 18, is now located at approximately the same level as the outer annular end face 50 of the connecting piece 22.

The O-ring 40 is pressed against the edge of the undercut 25 of the connecting piece 22 by the annular flange 36 of the sleeve 28 and compressed. The O-ring 40 thus compressed now exerts a pressure in the direction of the arrow 52 on the annular flange 36, and thus on the sleeve 28. This is a spring-loaded housing of sleeve 28 within connecting piece 22.

Figure 6:
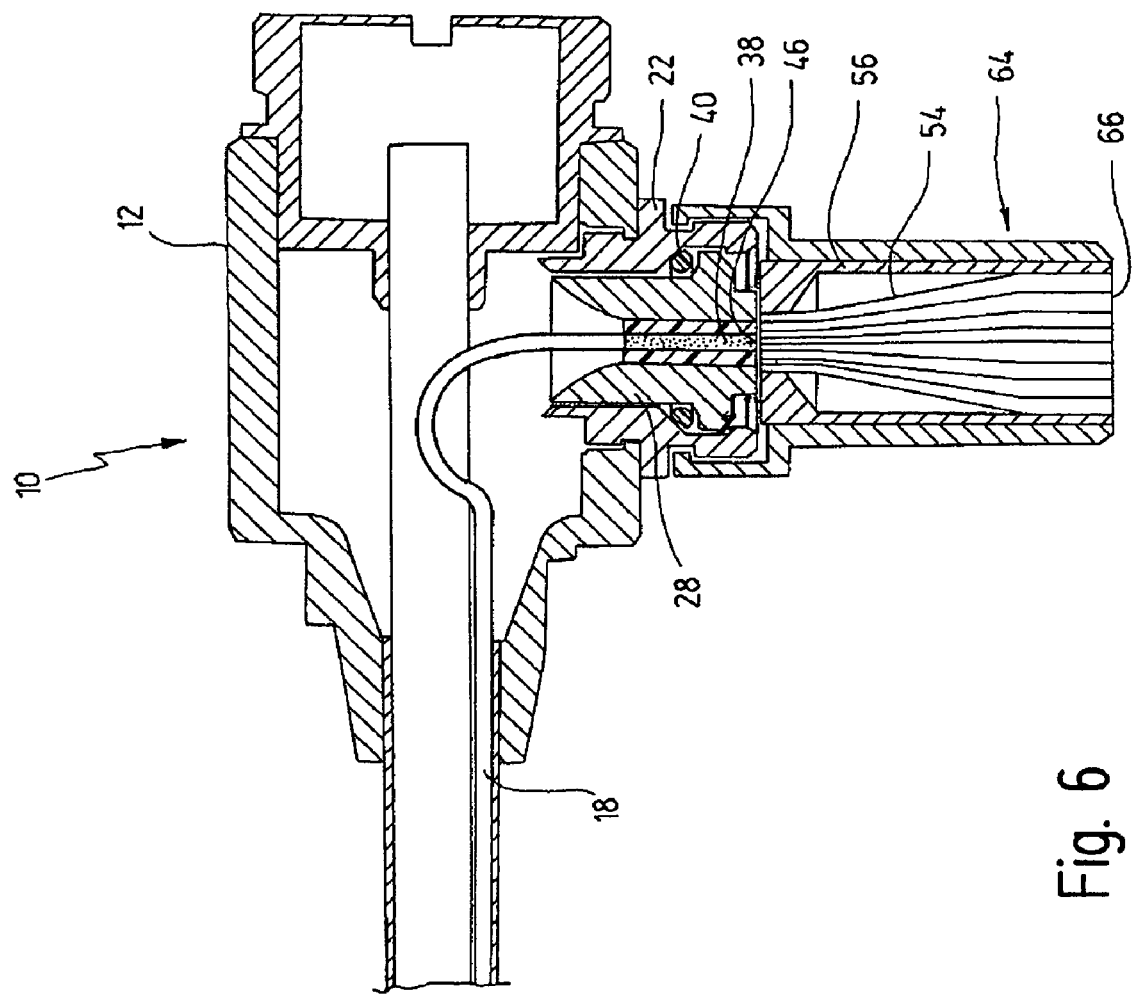
FIG. 6 shows the section of FIG. 5, a fiber cone having been fitted in a fashion bearing against the sleeve.

As illustrated in FIG. 6, a fiber cone 54 is arranged at the end surface 46 of the sleeve 28 or of the proximal end section 38 of the optical fibers 18.

The fiber cone 54 is held in a conical sleeve 56 that is screwed onto the outside of the connecting piece 22. A liquid cement is introduced into the conical sleeve 56 and also penetrates into the free spaces between the sleeve 28 and connecting piece 22. The liquid cement is cured in order to produce a tight connection.

The connecting piece 22, the sleeve 28, the proximal end section 38 of the optical fibers 18, the fiber cone 54 and the conical sleeve 56 together form a light connection 64 of the endoscope 10.

As is illustrated in FIG. 5 by the arrow 52, the O-ring 40 presses the sleeve 28 against the fiber cone 54 and thus ensures that the end surface 46 bears against the fiber cone 54 in as planar a fashion as possible.

In order to raise the efficiency of the transmission of light between the fiber cone 54 and the optical fibers 18, an optically conductive medium can be introduced between the fiber cone 54 and the end surface 46.

The light connection 64 is used to connect the endoscope 10 to an external light source that couples light into the fiber cone 54 over the entire width of the area of the conical section. This light is guided along the fiber cone 54, focused and coupled into the optical fibers 18 at the end surface 46 over a smaller diameter.

What is claimed is:

1. An endoscope comprising:
    a shaft,
    a head disposed at a proximal end of said shaft,
    a light connection provided at said head,
    optical fibers extending from said proximal light connection to a distal end of said shaft for guiding light from said light connection to said distal end, and
    having a sleeve in which a proximal end section of said light fibers is fixed, said sleeve is designed in such a way, that it can be introduced into a connecting piece of said light connection in a linear movement without turning it, and wherein said sleeve is axially movable in said connecting piece in a state when said endoscope is fully assembled,
    wherein said axially movable sleeve is captured within said connecting piece, and
    wherein a proximal end of said connecting piece has an annular flange at its inner side adjoined by an undercut, said sleeve is inserted into said connecting piece through said annular flange under pressure.

2. The endoscope of claim 1, wherein said axially movable sleeve cooperates with a resilient member in such a way that it is axially spring-loaded.

3. The endoscope of claim 2, wherein said resilient element is designed as an O-ring.

4. The endoscope of claim 1, wherein a fiber cone is arranged in a bearing fashion at a proximal end surface of said sleeve and said glass fibers contained therein.

5. The endoscope of claim 4, wherein an optically conductive medium is introduced between said proximal end surfaces and said fiber cone.

6. The endoscope of claim 1, wherein said proximal end section of said light fibers is fixed in said sleeve by an adhesive bonding.

* * * * *